(12) United States Patent
Aloy (10) Patent No.: US 6,452,624 B1
(45) Date of Patent: Sep. 17, 2002

(54) MEDICAL VIDEO ENDOSCOPY MONITORING DEVICE

(75) Inventor: Paul Aloy, Brussels (BE)

(73) Assignee: Omnilabo N.V., Brussels (BE)

( * ) Notice: Subject to any disclaimer, the term of this patent is extended or adjusted under 35 U.S.C. 154(b) by 0 days.

(21) Appl. No.: 09/485,718

(22) PCT Filed: Sep. 2, 1998

(86) PCT No.: PCT/BE98/00128

§ 371 (c)(1),
(2), (4) Date: Mar. 2, 2000

(87) PCT Pub. No.: WO99/12357

PCT Pub. Date: Mar. 11, 1999

(30) Foreign Application Priority Data

Sep. 2, 1997 (EP) .............................................. 97870129

(51) Int. Cl.[7] .............................. A61B 1/04; H04N 7/18
(52) U.S. Cl. .............................. 348/71; 348/74; 396/17; 600/109; 600/133; 600/160
(58) Field of Search ....................... 348/71, 74; 396/17; 300/109, 133, 160; H04N 7/18

(56) References Cited

U.S. PATENT DOCUMENTS

4,461,558 A * 7/1984 Tanikawa et al. ............. 396/17

* cited by examiner

Primary Examiner—Howard Britton
(74) Attorney, Agent, or Firm—Jacobson Holman, PLLC (57) ABSTRACT

A device for monitoring a use of a medical video endoscope (1), comprising a processing system (4) having an input for receiving color data signals (5), comprising a set of color data components, said processing system (4) comprising a color analysis unit (21), provided for selecting at least one of said color data components, and for determining for each of said selected color data components an intensity value, said processing system further comprising a memory (10–12) for storing at least a first color value reference range, indicating first color intensity values obtained upon use of said endoscope, said memory being connected to an input of a verification unit (25), said verification unit being provided for determining a second color value on the basis of said intensity values, and for verifying if said second value is within said first color value reference range, said verification unit being also provided for generating a flag, indicating said use, upon establishing that said second color value is within said first color value reference range.

10 Claims, 5 Drawing Sheets

MEDICAL VIDEO ENDOSCOPY MONITORING DEVICE

The invention relates to a device for monitoring if a medical video endoscope has been used for medical endoscopy purposes, said device comprises a processing system having an input for receiving colour data signals, comprising a set of colour data components generated by said endoscope during an endoscopy, said processing system comprising a colour analysis unit, provided for selecting at least one of said colour data components.

Such a medical video endoscope is known from the U.S. Pat. No. 4,901,143 and used for medical diagnostic purposes of for example the stomach and the lungs. Therefore the endoscope comes into contact with aggressive substances such as stomach acid and needs to be disinfected after use. The video endoscope comprises a camera, generally a CCD camera, and a light conductor which should not enter into contact with liquid substances such as water, blood, or acid, neither during a diagnostic use, nor during disinfection. The camera and the light-conductor are therefore located in a housing which should regularly be checked in order to detect an eventual leak. Under ideal operating conditions, the leak check should be realised after each use, in order to detect leaks and limit in such a manner the damages which could occur due to a leak.

As however a leak check is a time-consuming activity, it is often "overseen" by the medical personnel, who continues to use the endoscope without having performed the leak check and sometimes not the disinfection operation. A leak can however cause serious damages to the endoscope leading to substantial and sometimes frequent repair costs. Of course no disinfection of the endoscope could also lead to serious infections of the patients.

The actual endoscopes however are not provided with any means which could warn the user that the leak check and the disinfection operation have to be done after each use, as the use itself is not detected by the endoscope himself. At this stage one can only rely on the conscience of the medical personnel to perform the leak check and the disinfection operation in order to take care of the good health of the patients and the endoscope.

It is an object of the invention to realise a device for monitoring a use of a medical video endoscope, wherein the use of the endoscope can be checked, so that an indication can be given to the medical personnel that for example a leak check and a disinfection have to be performed, in order to take care of the well functioning of the endoscope and thus to save repair costs.

A device according to the present invention is therefore characterised in that said processing system is provided for determining for the, or each, of said selected colour data components, an intensity value, by measuring the intensity of the considered colour data component during a predetermined time period, said processing system further comprising a memory for storing at least a first colour value reference range, indicating first colour intensity values obtained by executing said endoscopy, said memory being connected to an input of a verification unit, having a further input for receiving said intensity value(s), said verification unit being provided for determining a second colour value on the basis of said intensity values, and for verifying if said second colour value is within said first colour value reference range, said verification unit being also provided for generating a flag, indicating said use, upon establishing that said second colour value is within said first colour value reference range. It has been established that the colour intensity of at least one of the colour data components, forming the picture recorded by the endoscope, changes considerably when the endoscope is entered into a human or animal body. The gist of the present invention is now to use the information of the colour intensity of at least one colour data components during a predetermined period for establishing the use of the endoscope. By verifying if the second colour value, which is derived from that colour intensity value, is within said first range, it can be established whether that second colour value represents a value corresponding with one indicating that the endoscope has been entered into a body and so if said endoscope was used. The generation of the flag thus indicates that the endoscope was used and can then for example trigger a warning signal for the medical personnel that a disinfection operation and leak check are required. As the attention of the personnel is drawn to the necessity of checking the well functioning of the endoscope, costs can be saved as damages could be detected at an early stage.

A first preferred embodiment of a device according to the present invention is characterised in that said colour analysis unit is provided for selecting at least a first and a second colour data component, said verification unit being provided for determining said second colour value by subtracting the intensity values of the first and second colour data component. As two colours are involved, of which the difference of their second colour value is considered, a more reliable result is obtained.

A second preferred embodiment of a device according to the present invention is characterised in that said colour data signal is a video Red, Green, Blue signal and wherein said first respectively second colour data component is the Red respectively Green signal. Red is a dominant colour in the endoscope picture when the latter is introduced into the body, whereas green is dominant outside the body.

Preferably said predetermined time period corresponds to at least a part of the period of one video frame. This facilitates the operation of the device as the synchronisation signals of the video pictures can be used.

A third preferred embodiment of a device according to the present invention is characterised in that said colour data signals are organised in successive pictures, said processing system being provided for performing said selection for each of said successive pictures, said verification unit being provided for outputting said flag. if said flag has been generated for a predetermined number of successive pictures. As now the analysis is performed over subsequent pictures, the error probability is substantially decreased.

A fourth preferred embodiment of a device according to the present invention is characterised in that said device comprises a leakage detection indicator, said leakage detection indicator comprises a further memory for storing said flags, and a time schedule indicating a time at which each of said flags were generated, said leakage detection indicator being provided for generating a leakage check signal on the basis of said flag, said time schedule and an actual time. The medical personnel thus receives an indication that a leakage check is required.

A fifth preferred embodiment of a device according to the present invention is characterised in that said device comprises a counter, provided for counting the number of generated flags. In such a manner the device according to the present invention can also be used for registering the use of the device and provide the necessary data for example in case the endoscope should be leased. The frequency at which the endoscope is used can be determined and several informations based on this frequency could be generated.

The present invention will now be described in more detail by means of a preferred embodiment illustrated in the drawings wherein

FIG. 2 (a+b+c) illustrate an example of the intensity of the different colour data components of an RGB signal produced by a camera of an endoscope and processed by the colour analysis unit;

In the drawings a same reference sign has been assigned to a same or analogous element.

Figure 1:
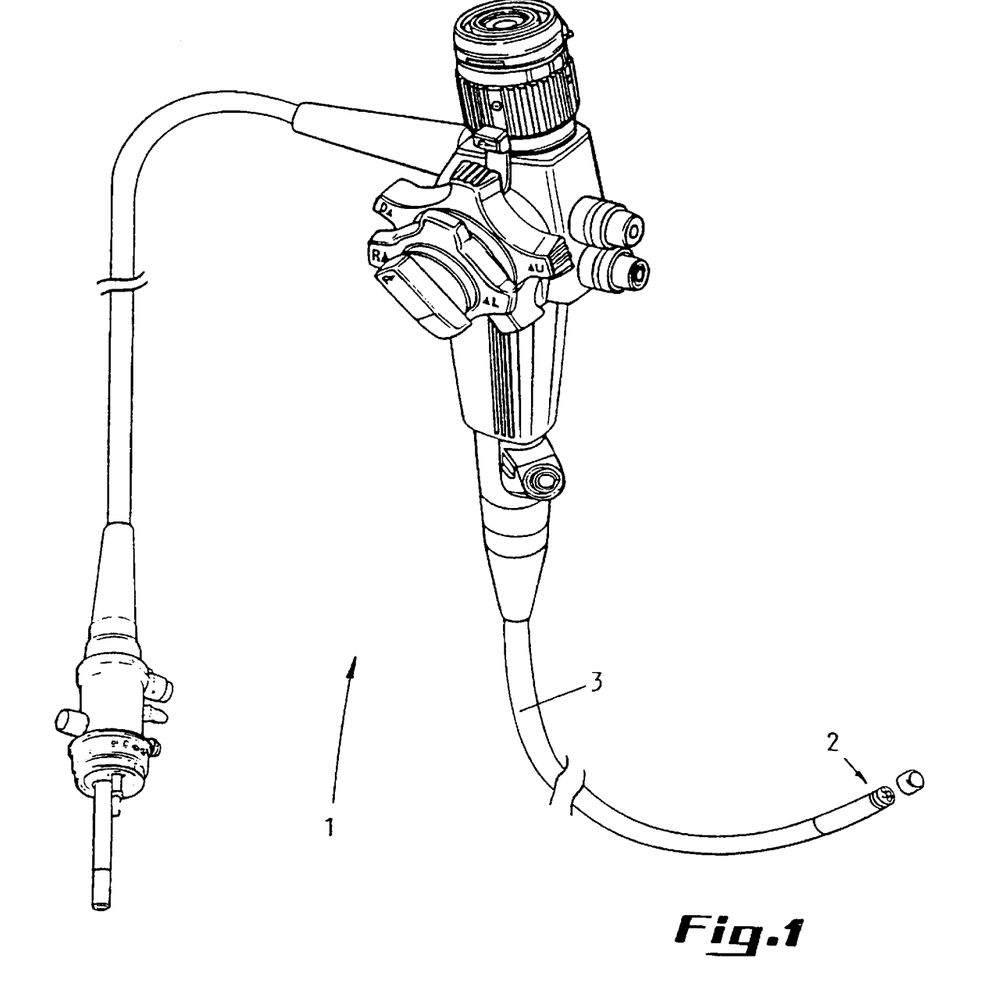
FIG. 1 illustrates an example of an endoscope.

FIG. 1 shows an example of a medical video endoscope which can be used for internal examination of a human or animal body. The endoscope 1 comprises a flexible part 3 and a head 2, wherein a camera, for example a CCD camera is housed. Within the flexible part, a light conductor, for example an optical fibre, is lodged. It is important that no liquid substances, present in the body on which the examination is applied, reach the light conductor, the CCD or any other internal part of the endoscope. Indeed the latter substances are sometimes aggressive, in particular stomach acid, and can therefore substantially damage the endoscope. Also the water and other liquid substances, used for disinfection of the endoscope, should not reach the internal part of the endoscope. The endoscope manufacturers therefore prescribe that after each examination a leak check should be performed, in order to enable an early detection of a leak and thus limit the damage and repair costs. For hygienic purpose the endoscope should also be disinfected after each use.

It should be noted that the present invention is not only applicable to flexible endoscopes, as rigid ones could also be considered. Leakage checks and disinfection procedures are only given as examples, but other applications such as registration of the use, establishing links between the user and the frequency the endoscope is used, are also possible.

The present invention now enables to monitor the use of the endoscope so as to give for example a warning to the medical personnel that a leak check and/or a disinfection operation have to be performed. For that purpose the colour data signals, generated by the camera of the endoscope are input into a device 4, for monitoring the use of the endoscope.

Figure 2A:
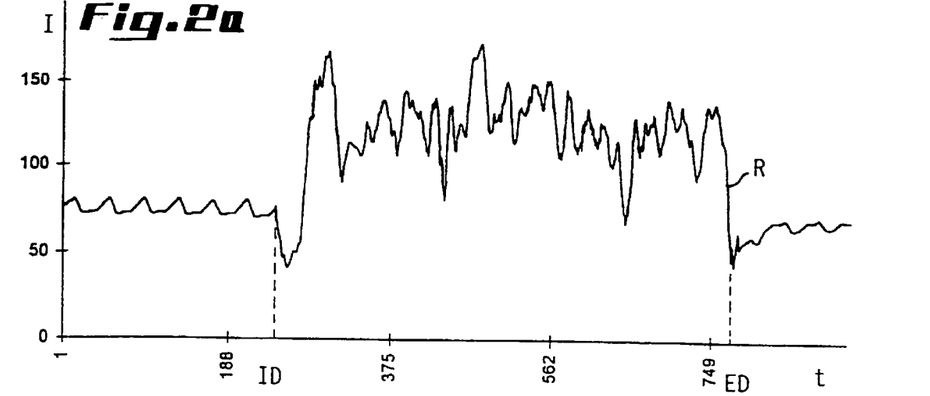
Figure 2B:
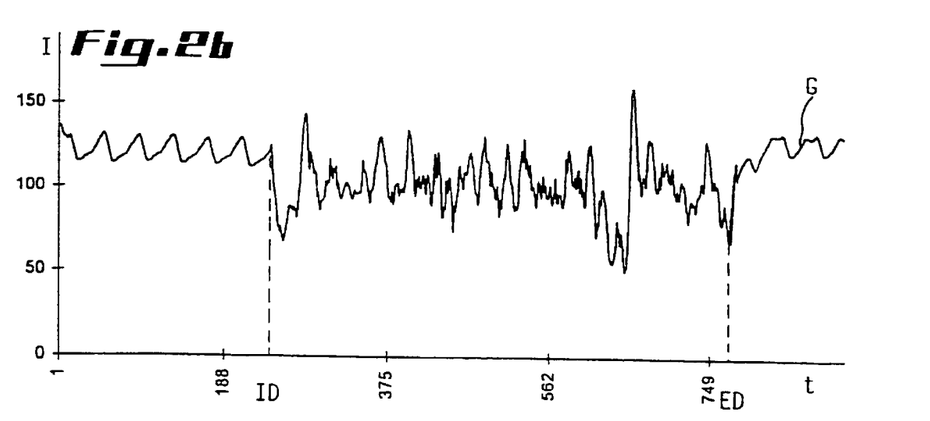
Figure 2C:
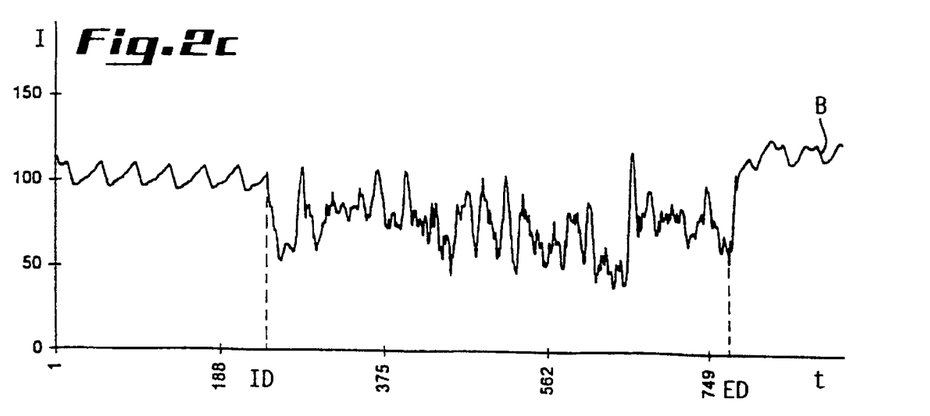

The device according to the present invention operates on the principle that an analysis of the colour data signals, produced by the camera of the endoscope, can be used in order to establish the beginning and the end of an examination such as for example a diagnosis. As can be seen in FIG. 2, wherein the intensity (I) of a red (R) (FIG. 2a), green (G) (FIG. 2b) and blue (B) (FIG. 2c) signal, produced by the endoscope camera and after processing by the colour analysis unit (21) is illustrated, that intensity varies in function of whether an examination is applied or not, i.e. whether or not the endoscope is introduced in the human or animal body. The intensity (I) is given as a function of time (t). Before the beginning of the examination, i.e. on the left hand side of the line ID, indicating the beginning of the examination, the intensity of the colour data component green (G) is the highest, whereas red (R) is the lowest. During examination, i.e. between the lines ID and ED (end of examination), the total intensity of the R component is higher than the one of the G or B component. After examination, the intensity of the R component drops to a substantially lower value, whereas the intensity of the G colour data component increases. By measuring for each picture, or for a plurality of successive pictures, the total intensity of at least one colour data component, for example the component R, it is possible to determine whether or not an examination has taken place.

In the given description, the colour components R, G and B were considered, as these are generally the ones produced by a video camera. It will however be clear that the present device could also operate with a different colour data signal such as for example a YMCK signal. The colour data signals are supplied either as digital or as analog data. For the present invention it is important that the colour data signal comprises a set of colour data components on which an analysis can be performed. The analysis, based on the colour intensity of the components, can be realised either on a single component or on a combination of two or more components.

In the description of the present invention, given hereunder, use will be made of a calculation of the difference (R−G) in intensity between the components R and G, for clarity's sake. However other combinations such as for example R−(G+B) or $R^2-G^2$ could also be used, depending on the used or selected colours.

Figure 3:
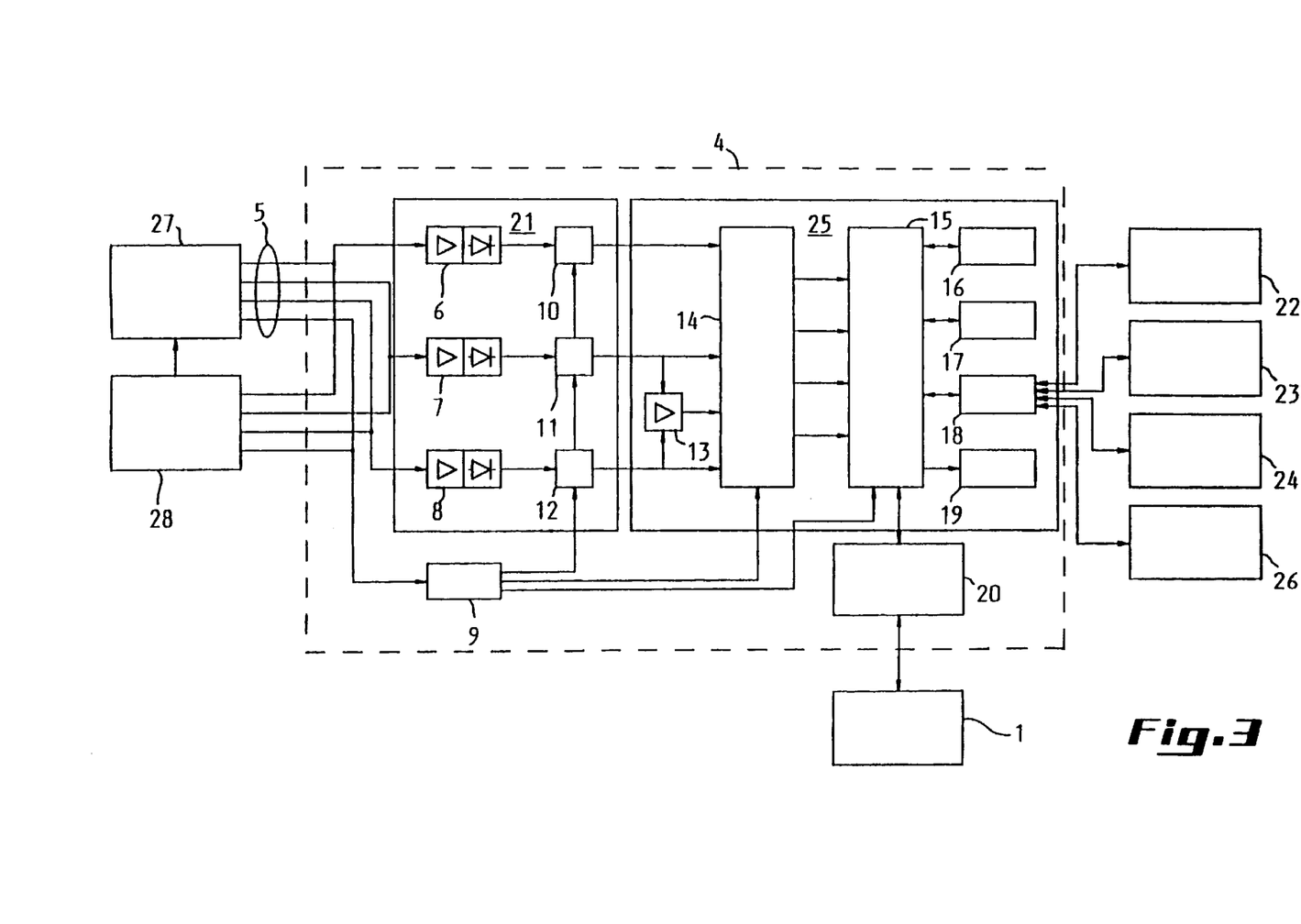
FIG. 3 illustrates schematically the electronic circuit of a device according to the invention.

FIG. 3 shows schematically an embodiment of an electronic circuit for a processing system as part of a device according to the present invention. The processing system 4 comprises an input 5, for receiving the colour data signals, which comprise the RGB colour data components and the synchronisation (S) signal. The colour data components, originating from the RGB colour converter 27 of the endoscope and his processor 28, are supplied to a colour analysis unit 21, which comprises for each colour data component a series connection of an amplifier-rectifier (6, 7, 8) and a first memory (10, 11, 12). Instead of using such a series connection, an accumulator could also be used. The synchronisation signal is presented to a trigger pulse generator 9, which first output is connected to a control input of the first memories 10, 11 and 12.

The trigger pulse generator 9 is provided for generating read and write signals, to be supplied to the first memories. The trigger pulse generator is programmable in such a manner as to consider either the whole picture information or only a part of it. That part could be formed either by a set of pixels forming a single cluster or a set of clusters distributed over the picture. For example in the case of interlaced video frames, only one of both frames could be considered, such as to leave time for further calculation. Also only a predetermined number of lines of a line-wise built-up picture could be used, for example in the case where the picture produced by the endoscope only covers a part of the screen of a monitor. Alternatively, instead of considering each time only a single picture, different subsequent pictures could be used. The trigger pulse generator comprises for example one or more counters and the output trigger signals are generated by the counters, reaching a predetermined number of count synchronisation pulses.

Each amplifier-rectifier 6, 7 and 8 is provided for transforming the received AC signal into a DC signal and for integrating the DC signal. For each selected colour data component, the total intensity of the considered colour within the received picture is determined. Under control of the trigger Ti signal, received by the first memories 10, 11 and 12 and produced by the trigger pulse generator 9, after lapse of the considered time period, for example one frame, the intensity value such as indicated by the amplifier-rectifier, will be stored in the respective first memories. The reading of the amplifier-rectifier 6, 7 and 8 will also cause their reset so that a new counting cycle can be started. Alternatively the amplifier-rectifier could be reset by the vertical synchronisation pulses. The first memories 10, 11 and 12 now stores for the respective colours blue B, red R and green G an intensity value (Ib, Ir, Ig), indicating the total intensity of the respective colour, during the considered time period.

The output of each of the first memories 10, 11 and 12 is connected to a verification unit 25, comprising buffer 14, which also receives the difference signal, formed by the subtracting member 13, which is part of the verification unit. The latter having inputs connected with respective outputs of the first memories 11 and 12. The subtracting member 13 thus receives the intensity values of the colours red and green (Ir and Ig), in order to determine the value Ir–Ig. The buffer 14 has a control input for receiving a trigger signal T2, generated by the trigger pulse generator 9. Trigger signal T2 is for example generated after lapse of a predetermined time period after generation of T1.

An output of the buffer 14 is connected to an input of a microprocessor 15. Further inputs of the microprocessor are connected with a ROM 16, a RAM 17, an I/O interface 18, a monitor screen 19 and a recognition unit 20, provided for recognition of the serial number of the endoscope. The ROM stores a series of first colour value reference ranges, indicating first colour values obtained upon use of the endoscope 1. For example for the colour component red R, respectively green G, and for the difference between red and green, first colour intensity value reference ranges I {R}, I {G} and I {(R–G)} are stored in the memory ROM 16. The RAM is used as operational memory for the microprocessor, whereas the I/O interface provides a communication of the processing unit with annexed peripherals such as a disinfector 22, a mainframe 23, an endoscope leakage checking unit 24 and further peripheral units 26, such as for example a video recorder.

The annexed peripherals are provided for transmitting information to the micro-processor 15. So for example, when a disinfection or leak test has been performed, the disinfector 22 or the leakage checking unit 24, sends a message to the micro-processor, indicating that the latter operation has been performed. This message is then stored in the RAM 17 under control of the micro-processor. Upon starting an examination with the endoscope, the verification unit 25 can then be addressed, in order to verify if disinfection or leak test messages are stored in the RAM 17. A disabling of the endoscope could then be initiated by the micro-processor if such messages are not stored in the RAM 17.

The verification unit 25 is provided for receiving the intensity values Ir, Ig, Ib, which are used to determine a second colour value, which is either equal to the considered intensity values or derived therefrom, such as the difference signal Ir–Ig formed by the subtractor 13, which is part of the verification unit 25. One or several of those second colour values will be used to verify if they are within the first colour intensity value reference range, stored in the ROM. For example for the value Ir, it could be verified if it is within the range I {R}. If the latter is the case, this signifies that the intensity of the colour data component in the considered picture is such that the endoscope was used for diagnostic purpose. If on the other hand Ir is not within I {R}, then the endoscope was not introduced into a body. If the verification unit establishes that Ir is within I {R}, it generates a flag which is then memorised in RAM 17 and, if required, displayed on the monitor screen 19.

In order to obtain a more reliable result, preferably the second colour value Ir–Ig is used, and the range I {(R–G)} is considered. Upon considering Ir–Ig, a noise filtration is realised on the signal so that the influence of the noise on the signal is reduced. Moreover Ir–Ig enables to distinguish more clearly a transition between an examination and a non-examination. Reverting to FIG. 2, it can be seen that Ir–Ig is positive during an examination, and negative when no examination is done. A transition between a positive and a negative value of Ir–Ig thus indicates an examination.

As video pictures are concerned, which are formed by successive pictures, the reliability of the device can further be improved by considering a series of successive pictures and generating the flag only when for a predetermined number of pictures it has been established that a diagnosis is performed. For that purpose the verification unit receives a third trigger signal T3, generated by the trigger pulse generator and derived for example of the vertical synchronisation signal. The verification operation is performed for each of the successive pictures and each time that a flag is generated, a counter position is modified. The value indicated by that counter will then form a parameter, on the basis of which it can be decided whether or not an examination has been performed.

Figure 4:
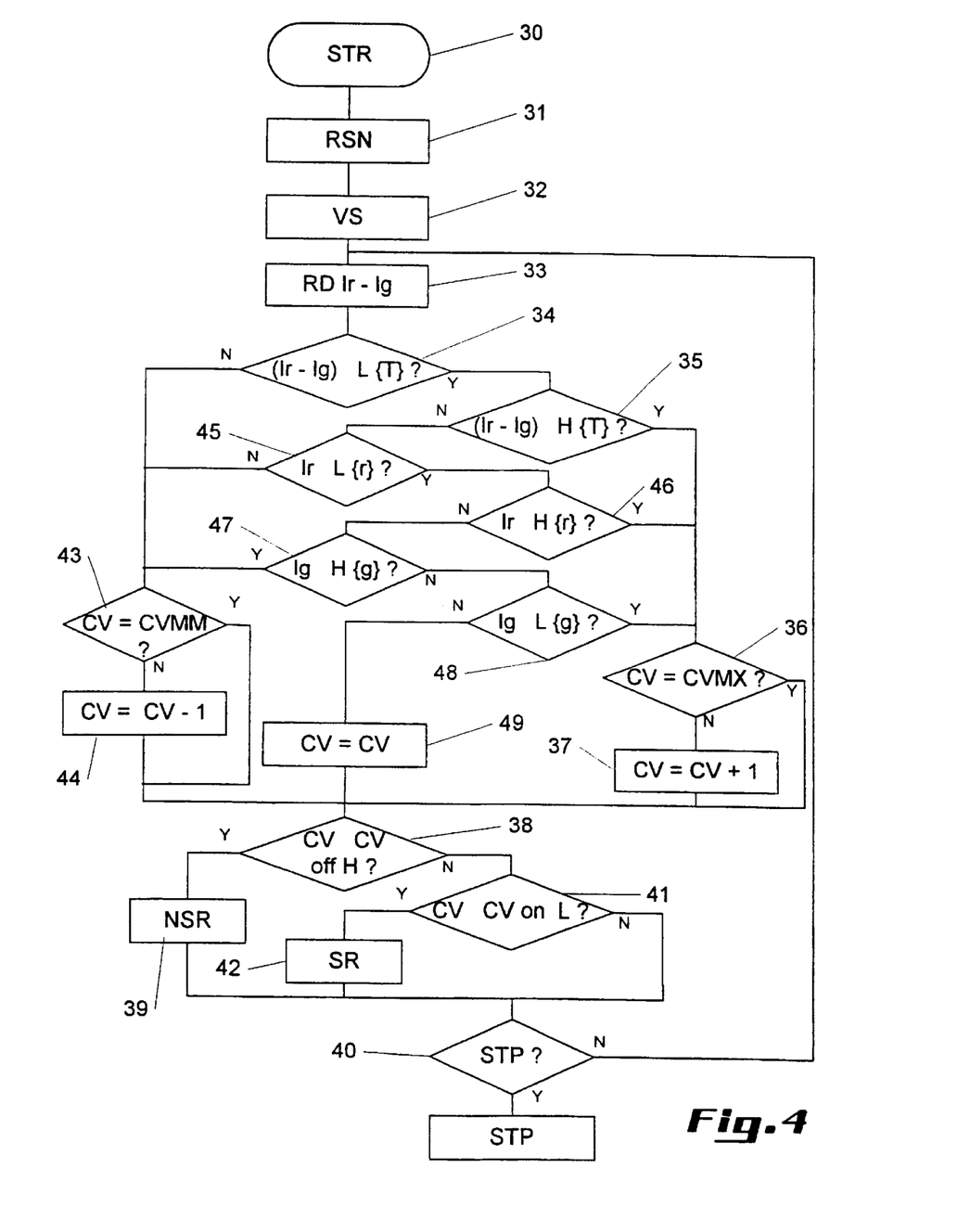
FIG. 4 shows a flow chart of a routine for checking if the endoscope is used for diagnostic purpose.

In order to avoid that erroneous intensity values lead to incorrect interpretation, the verification unit is further provided with interpretation means of which the operation will be described by means of the flow chart illustrated in FIG. 4. The different steps of this flow chart are for example stored by means of a computer program in the RAM and are executed under control of the microprocessor 15. The different steps will now be described.

30 STR: the video endoscopy system is started.

31 RSN: the serial number of the endoscope is read by means of the ID number recognition unit 20 and stored in the RAM 17.

32 VS : the video endoscopy monitoring system is initialised and thereafter RGB signals are input into the monitoring device via input 5.

33 RD Ir–Ig the values Ir, Ig, Ib and the second colour value Ir–Ig are read and memorised for the considered picture.

34 (Ir–Ia)>L {T}?: there is verified if (Ir–Ig) is higher than a threshold value L {T} (see FIG. 6a) indicating a minimum threshold value for Ir–Ig. L {T} represents a value for which it can certainly be concluded that if (Ir–Ig)≦L {T} no examination takes place.

35 (Ir–Iq)>H {T}?: there is verified if (Ir–Ig) is higher than a threshold value H {T} (FIG. 6a) indicating a minimum threshold value for which it can certainly be considered that an examination takes place.

Figure 6:
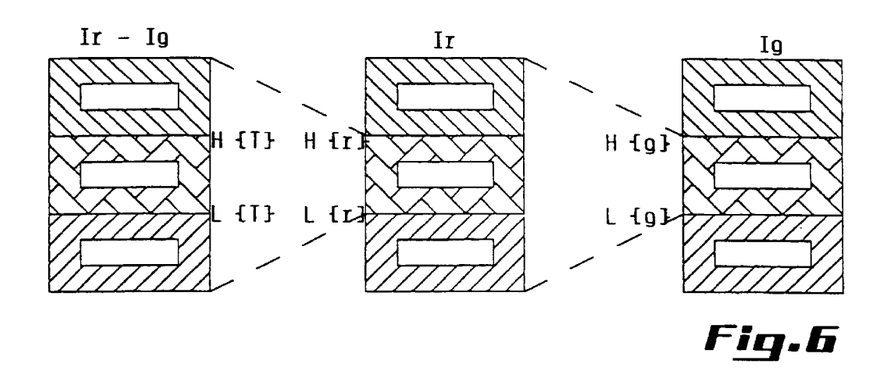
FIGS. 6 and 7 illustrate a series of ranges used to realise the check routine.

As can be seen in FIG. 6a H {T}>L {T} which signifies that between H {T} and L {T} there is a range for Ir–Ig for which it can not be concluded with certainty that an examination takes place.

Figure 7:
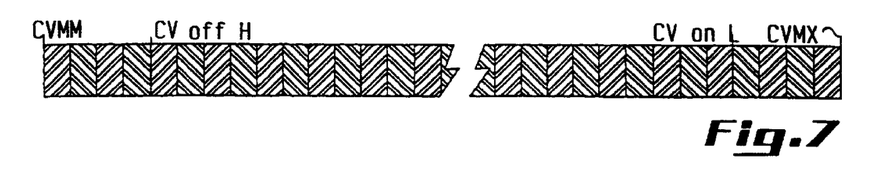

36 CV=CVMX?: there is verified if a counter value CV has reached his maximum value CVMX (see FIG. 7). This parameter CV indicates the number of times that a flag indicative of an examination has been generated.

37 CV=CV+1: if the counter value CV has not reached his maximum value CVM and a flag has been generated [(Ir–Ig)>H {T}] the counter value is increased with one unit.

38 CV<CVoffH?: there is verified if the counter value CV is lower than a minimum threshold value CVoffH. This minimum threshold value indicates the amount of flags that has to be generated in order to accept that an examination has indeed been stopped.

39 NSR: if CV<CVoffH then no diagnosis is started.
40 STP?: it is verified if the operation of the endoscopy system was stopped.
41 CV>CVonL?: it is verified if the value CV has reached a first intermediary value CVonL indicative of a start of an examination.
42 SR: if CV>CVonL then an examination is started.
43 CV=CVMM: there is verified if the value CV has reached an absolute minimum value CVMM indicative of that no examination takes place.
44 CV=CV−1: the CV value is decreased with one unit as it has been established that no examination occurs.
45 Ir>L {r}?: when the value Ir−Ig is situated in the range between L {T} and H {T}, another intensity value, namely Ir is considered. There is verified if Ir>L {r} wherein L {r} is a lower threshold value (see FIG. 6b) for the intensity value Ir. If Ir<L{r} then step 43 is executed because it indicates that no examination is realised.
46 Ir>H {r}?: there is verified if Ir>H {r} wherein H {r} is an upper threshold value for the intensity value Ir indicating that the red colour data component has passed an intensity value which belongs to an examination. If Ir>H {r}? then step 36 is executed, because it indicates the probability that an examination is realised.
47 Ig>H {g}?: if the value of Ir is situated in the range between L {r} and H {r}, then the colour component green is considered. As can be seen in FIG. 2, if the colour data component becomes dominant, it indicates that no examination occurs. There is verified if the intensity value Ig>H {g} wherein H {g} is an upper limit for the colour green indicating that no examination occurs.
48 Ig<L {g}?: there is verified if Ig<L {g} wherein L {g} is a lower intensity threshold value beneath which there is a large probability that an examination occurs.
49 CV=CV: if Ig is in the range between L {g} and H {g}, there can not be concluded whether or not there is an examination. Therefore the counter value CV remains unchanged.

Figure 5:
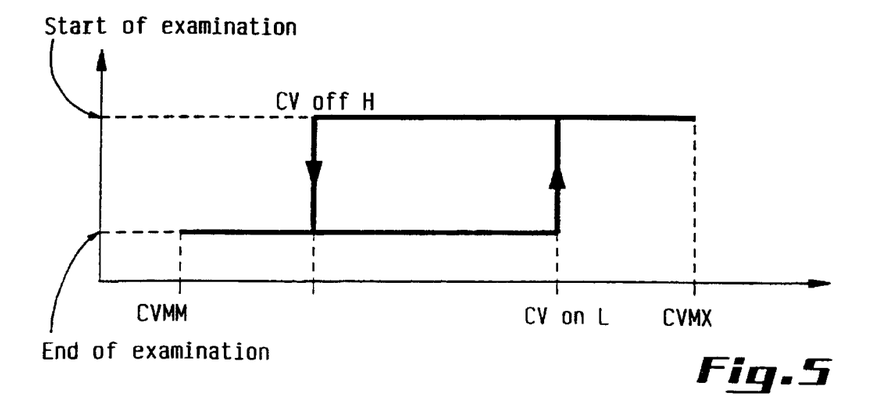
FIG. 5 illustrates a hysteresis as part of the check routine.

As is illustrated in FIG. 5, wherein the value CVMM, CVonL, CVMX and CVoffH are represented in a different manner, a hysteresis is built in the counter value check. The decision that an examination has started is only taken if CV>CVonL (step 41), whereas the decision that no examination was started is only taken when CV<CVoffH. As CVoffH<CVonL, there is a hysteresis in the graph shown in FIG. 5, which enables to take the decision in a reliable manner, so that the flag is output to the I/O interface with a large reliability.

The described embodiment based on an analysis of the value Ir−Ig>0 is based on the fact, that it is the introduction of the endoscope into the body which is monitored. Of course other alternatives such as for example Ig−Ir>0, which occurs outside the range ID−ED (FIG. 2) could be used as basis of the analysis. Further all the intensities Ir, Ig, Ib could be used.

As already described, the flag indicating that the endoscope has been used, can serve to draw the attention of the medical personnel that i.a. a leakage check is required. For that purpose the device comprises a leakage detection indicator, comprising for example the RAM 17 and a display, which can be the monitor screen 19 or a led. The flags, generated during the examination, are stored in RAM 17 as well as a time schedule, indicating a time at which each of the flags were generated. The leakage detection indicator is provided for generating a leakage check signal, taking into account the stored flags, the time at which they were generated and the actual time. So for example, if an examination was done from 9.00 o'clock till 9.15 o'clock, and a subsequent is started at 10.00 clock, a leakage signal will be output because too much time has lapsed since the last examination. The RAM 17 is reset if the leakage checking unit 24 produces a result signal, indicating that the leakage check was performed and that the endoscope is leak free.

The device according to the invention is further not limited to generate a warning signal for leakage check or disinfection purpose. The generated flag could also be used for other purposes, such as input data for lease purpose, user identification, maintenance check etc.. Instead of buying the endoscope, the medical instances could lease an endoscope and pay an amount for each use. As the number of generated flags provides an information as to how many times the endoscope has been used, this information could then serve to calculate the due amount according to the lease contract. As the serial number of the endoscope can be read and identified by means of the ID number recognition unit 20, for each serial number the amount of generated flags could be separately stored and read.

The endoscopic system could also request the user to identify himself, so that statistics could be established, if for each user the number of flags are individually stored.

If the number of flags exceeds a predetermined amount, indicating that maintenance is required, the device could issue a maintenance request signal.

What is claimed is:

1. A device for monitoring if a medical video endoscope has been used for medical endoscopy purposes, said device comprises a processing system (4) having an input (5) for receiving colour data signals, comprising a set of colour data components generated by said endoscope during an endoscopy, said processing system comprising a colour analysis unit (21), provided for selecting at least one of said colour data components, characterised in that said processing system is provided for determining for the, or each, of said selected colour data components, an intensity value, by measuring the intensity of the considered colour data component during a predetermined time period, said processing system further comprising a memory (16) for storing at least a first colour value reference range, indicating first colour intensity values obtained by executing said endoscopy, said memory being connected to an input of a verification unit (25), having a further input for receiving said intensity value(s), said verification unit being provided for determining a second colour value on the basis of said intensity values, and for verifying if said second colour value is within said first colour value reference range, said verification unit being also provided for generating a flag, indicating said use, upon establishing that said second colour value is within said first colour value reference range.

2. A device as claimed in claim 1, characterised in that said colour analysis unit (21) is provided for selecting at least a first and a second colour data component, said verification unit being provided for determining said second colour value by subtracting the intensity values of the first and second colour data component.

3. A device as claimed in claim 2, characterised in that said colour data signal is a video Red, Green, Blue signal and wherein said first respectively second colour data component is the Red respectively Green signal.

4. A device as claimed in claim 3, characterised in that said predetermined time period corresponds to at least a part of the period of one video frame.

5. A device as claimed in claim 1, characterised in that said colour data signals are organised in successive pictures, said processing system being provided for performing said selection for each of said successive pictures, said verification unit (25) being provided for outputting said flag, if said flag has been generated for a predetermined number of successive pictures.

6. A device as claimed in claim 1, characterised in that said device comprises a leakage detection indicator, said leakage detection indicator comprises a further memory for storing said flags and a time schedule indicating a time at which each of said flags were generated, said leakage detection indicator being provided for generating a leakage check signal on the basis of said flag, said time schedule and an actual time.

7. A device as claimed in claim 6, characterised in that it comprises a further input for receiving a result signal, issued by a leakage checking unit (24), said leakage detection indicator being provided for resetting said memory upon receipt at said further input of a result signal indicating that said endoscope is leak free.

8. A device as claimed in claim 1, characterised in that said device comprises a disinfection warning, said disinfection warning comprises a further memory for storing said flags, said disinfection warning being provided for generating an infection check signal on the basis of said flag.

9. A device as claimed in claim 1, characterised in that said device comprises a counter, provided for counting the number of generated flags.

10. A device as claimed in claim 9, characterised in that said counter is provided for generating a control signal upon indication of a predetermined counting number.

* * * * *